(12) United States Patent
Kaminski et al.

(10) Patent No.: US 8,507,284 B2
(45) Date of Patent: Aug. 13, 2013

(54) METHOD AND APPARATUS FOR EXTRACTION OF STRONTIUM FROM URINE

(75) Inventors: Michael D. Kaminski, Lockport, IL (US); Carol J. Mertz, Downers Grove, IL (US); Ilya A. Shkrob, Chicago, IL (US); Mark L. Dietz, Evanston, IL (US); Cory A. Hawkins, Shorewood, WI (US)

(73) Assignee: UChicago Argonne, LLC, Chicago, IL (US)

( * ) Notice: Subject to any disclaimer, the term of this patent is extended or adjusted under 35 U.S.C. 154(b) by 159 days.

(21) Appl. No.: 13/182,873

(22) Filed: Jul. 14, 2011

(65) Prior Publication Data

US 2013/0017613 A1    Jan. 17, 2013

(51) Int. Cl.
*G01N 33/20* (2006.01)
*B01D 15/00* (2006.01)
*B01D 37/02* (2006.01)
*C01F 11/00* (2006.01)

(52) U.S. Cl.
USPC .......... 436/79; 436/73; 436/74; 423/2; 423/3; 423/157; 210/749

(58) Field of Classification Search
USPC .................. 436/73, 74, 79, 81, 82; 423/2, 3, 423/157; 210/749
See application file for complete search history.

(56) References Cited

U.S. PATENT DOCUMENTS

| | | | | |
|---|---|---|---|---|
| 5,100,585 A | * | 3/1992 | Horwitz et al. | 423/2 |
| 5,110,474 A | * | 5/1992 | Horwitz et al. | 588/20 |
| 5,281,631 A | | 1/1994 | Horwitz et al. | |
| 5,346,618 A | * | 9/1994 | Horwitz et al. | 210/198.2 |
| 5,449,462 A | | 9/1995 | Horwitz et al. | |
| 5,539,003 A | | 7/1996 | Horwitz et al. | |
| 5,582,737 A | * | 12/1996 | Gula et al. | 210/673 |
| 6,436,294 B2 | * | 8/2002 | Lundquist | 210/674 |
| 6,511,603 B1 | * | 1/2003 | Dietz et al. | 210/685 |
| 2006/0025713 A1 | | 2/2006 | Rosengart et al. | |

OTHER PUBLICATIONS

A. Raman et al., Validation of Deuterium-Labeled Fatty Acids for the Measurement of Dietary Fat Oxidation During Physical Activity, Jour. of Lipid Research 45, 2339-2344(2004).

(Continued)

*Primary Examiner* — Krishnan S Menon
*Assistant Examiner* — Dwan A Gerido
(74) *Attorney, Agent, or Firm* — Olson & Cepuritis, Ltd.

(57) ABSTRACT

The present invention provides an apparatus and rapid methods for extracting strontium ions from urine to provide a concentrated and purified strontium-90 extract suitable for scintillation measurements. The methods remove organic compounds, pigments, and alkali metal ions that can interfere with quantitative determination of strontium-90 in urine. A method of the invention comprises acidifying urine and removing organic pigments therefrom, loading a known quantity of so-treated urine onto a diphosphonic acid-based ion-exchange resin; flowing aqueous methanesulfonic acid through the diphosphonic acid-based ion-exchange resin to elute alkali metal ions therefrom; eluting strontium ions off of the diphosphonic acid-based resin and on to a strontium extraction chromatographic resin with a concentrated aqueous nitric acid solution; subsequently flowing water or a dilute acid stripping solution through the strontium extraction resin to strip the strontium from the strontium extraction resin; and collecting the strontium-containing stripping solution eluting from the strontium extraction resin.

7 Claims, 10 Drawing Sheets

(56) References Cited

OTHER PUBLICATIONS

T. Thorsen et al., Doubly Labeled Water Analysis Using Cavity Ring-Down Spectroscopy, Rapid Commun. Mass Spectrom, vol. 25, 3-8 (2011).

V. Scasnar, Determination of Strontium-90 in Urine by Extraction Without Ashing, Analytical Chem. vol. 56, 605-608 (1984).

J. Cobb et al., Determination of Strontium-90 in Water and Urine Samples Using Ion Chromatography, Analyst, vol. 119, 1759-1764 (1994).

A. Alvarez et al., Method for Actinides and Sr-90 Determination in Urine Samples, Appl. Radiat. Isot. vol. 47, 869-873 (1996).

S.L. Maxwell, III, Rapid Analysis of Emergency Urine and Water Samples, Journal of Radioanalytical and Nuclear Chemistry, vol. 275, 497-502 (2008).

A. Alvarez et al., New Method for 90Sr Determination in Liquid Samples, Journal of Radioanalytical and Nuclear Chemistry, vol. 191, No. 2, 315-322 (1995).

E. P. Horwitz, Extraction Chromatography of Actinides and Selected Fission Products: Principles and Achievement of Selectivity, www.eichrom.com, Radiochemistry (2010).

E. P. Horwitz, Solvent Extraction and Ion Exchange, vol. 10, 313-336 (1992).

* cited by examiner

METHOD AND APPARATUS FOR EXTRACTION OF STRONTIUM FROM URINE

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to extraction of strontium ions from urine. More particularly, this invention relates to methods and apparatus for extracting strontium ions from urine and determining the concentration of strontium in urine.

BACKGROUND

Strontium-90 ($^{90}$Sr), which is present in radioactive fallout, has a half-life of approximately 29 years (typically reported at values ranging from 28.5 to 29.1 years), and decays by high energy electron emission (β particle emission). Strontium-90 ions can be detected in the urine of subjects exposed to such fallout. Strontium tends to migrate to human bone structures, replacing calcium, and once absorbed, is difficult to eliminate. Long term accumulation of $^{90}$Sr has been shown to produce bone cancer.

Quantifying the ingestion of radioactivity is difficult. Biological indicators are only useful in the most extreme of exposures since the body can tolerate large doses of radioactivity. For some radionuclides that emit high energy gamma rays, one can use specialized radioactive counters that can count the entire human body. For radionuclides that emit alpha or beta particles or low energy gamma rays only, this type of counting is useless. Moreover, these facilities are few and far between and only available at very specialized centers. The standard technique is to analyze urine since the blood-urine pathway is common to all ingestions.

Health physicists use methods to quantify the dose burden to the body based on quantities measured in urine after a known number of days following exposure. The methods are based on gamma or beta-alpha counting of urine samples. For quantifying gamma-emitting isotopes (e.g., $^{137}$Cs) direct counting of urine samples works well since the gamma ray is able to easily transmit through the urine, the vial, and penetrate the active region of the detector. For beta-emitters like $^{90}$Sr or alpha emitters like many of the actinide isotopes, the standard method is liquid scintillation counting.

In liquid scintillation, an aliquot of the liquid sample is dissolved into a scintillation cocktail solution, which is a specially formulated solution that converts the beta and alpha ray energies into visible light pulses that are captured by the detector. Such scintillation solutions are well known in the art. However, care must be taken to quantify the quenching factor of such solution-cocktail mixtures. Quenching of radiation-induced luminescence of the fluorophores of the cocktail reduces the overall number of photons that reach the detector below the expected value based on total radioactive decay events. Both colored and non-colored materials can quench a sample. Certain electronegative species in solution can chemically disrupt the energy conversion process and eliminate the formation of the visible light pulse that is used for detection. Colored materials in solution can absorb or scatter the light pulse before it escapes from solution, thereby preventing its detection. Acidified urine is particularly troublesome because it contains both colored and colorless quenching agents. As a result, to count $^{90}$Sr (pure beta emitter) by the standard method (liquid scintillation counting), the $^{90}$Sr must be purified from the urine. The method for purification must separate the $^{90}$Sr from the organic and other chemicals dissolved in the urine, and also the other radioactive and non-radioactive ions that are present. The non-radioactive ions need to be removed for practical reasons since they will usually overload a separations column and prevent the $^{90}$Sr from being purified. To add difficulty, $^{90}$Sr decays to a very short lived daughter isotope $^{90}$Y that also emits a beta-particle. Because the $^{90}$Y is so short-lived, the number of radioactive emissions (beta emissions) is comparable to the number of $^{90}$Sr emissions. So, if an analytical method does not separate the $^{90}$Y from the $^{90}$Sr, the total counts by liquid scintillation will be grossly over-estimated and so will the resulting dose burden that is calculated. Radioactive $^{40}$K presents a similar problem, because it is present as a trace isotope of natural potassium in the urine.

Normal human urine is an aqueous solution containing a number of organic materials (e.g., urea, creatinine, uric acid and smaller amounts of carbohydrates, enzymes, fatty acids, hormones, pigments, mucins, etc.) and ions (e.g., sodium, potassium, calcium, etc.) that can vary greatly between individuals and is highly dependent upon diet. In addition, typical concentrations of metal ions in urine are high (e.g., about 0.1 M Na$^+$, 0.03 M K$^+$, and 0.005 M Ca$^{2+}$) compared to the trace quantities of strontium that might be found in urine samples. Thus, any practical method for extracting $^{90}$Sr from urine would require high capacity (where selectivity toward strontium is poor) or high selectivity (where the quantity of the extractant must be kept low). In practice, experimental protocols generally involve precipitation of alkaline earth metal ions from the urine and ashing of the precipitate to eliminate organic molecules, followed by elemental separations. This process is time-consuming, and requires a skilled technician, but is necessary to ensure quantitative recovery of strontium. However, when many samples have to be analyzed quickly, such as after a massive release of radioactive material, quantitative recovery of strontium may not be of primary importance, so long as one can ensure good, predictable recovery with a faster method.

Elimination of the ashing step in the prior reported methods has been proposed. In one reported alternative method, urine was diluted 5-fold with 0.1 M aqueous HNO$_3$ with about 1% of a poly(ethylene glycol) added, and solvent extraction with the acidic form of dicarbolide in nitrobenzene provided a high strontium distribution coefficient (D(Sr) >300) and high strontium selectivity over sodium (D(Sr)/D (Na)>800). The number of steps involved for extraction and purification is relatively high, and such solvent extraction methods are not readily scalable for large numbers of samples. The Center for Disease Control (CDC) has expressed a desire for a target analysis throughput of 10,000 samples per day using minimal operator assistance. Thus, any technique for strontium analysis for use by CDC must involve reusable equipment, and be rapid, automated, and predictable.

Attempts to concentrate and purify $^{90}$Sr from urine using a single strontium ion extraction chromatographic resin (also referred to herein as a "strontium extraction resin") have been hampered by the other ionic components of urine, particularly alkali metal ions which are present in much higher concentrations (e.g., 40 to 100 mM) than strontium (typically less than 10 picomolar, pM). Removing quenchers and/or separating the strontium from the quenchers and materials that interfere with Sr isolation (e.g., alkali metal ions) can be cumbersome and time consuming. Consequently, there is an ongoing need for new methods for rapidly and efficiently extracting and concentrating strontium from urine so that $^{90}$Sr concentrations can be determined without interference from other components found in urine. The present invention addresses this need.

SUMMARY OF THE INVENTION

The present invention provides methods and apparatus for rapidly extracting strontium ions (e.g., $^{90}$Sr$^{2+}$) from urine and determining the strontium concentration in the urine (e.g., human urine). One method embodiment of the present invention comprises the steps of (a) pretreating a sample of urine by acidifying the urine to a pH of less than about 2 with methanesulfonic acid (MSA) and removing scintillation-interfering materials (e.g., organic materials and pigments) from the urine (e.g., by agitating the acidified urine with activated carbon, and separating the activated carbon from the urine); (b) loading a known quantity of the pretreated urine (e.g., 10 to 30 column volumes) onto a column of a preconditioned diphosphonic acid-based ion-exchange resin (DP-resin) comprising diphosphonic acid groups and sulfonic acid groups bound to a particulate polymeric matrix; (c) introducing a flow of aqueous MSA through the diphosphonic acid-based ion-exchange resin, wherein the flow of aqueous MSA has a concentration (e.g., about 0.01 to about 2 M) and volume (e.g., about 10 to 30 column volumes) sufficient to reduce the concentration of alkali metal ions from the urine eluting from the DP-resin to about 10 mM or less; (d) introducing a flow of aqueous nitric acid though the DP-resin, wherein the flow of aqueous nitric acid has a concentration (e.g., about 1 to about 10 M) and volume (e.g., about 2 to 5 column volumes) sufficient to elute off at least about 85 mole percent (preferably at least about 90, 95, 98 or 99 mole percent) of any strontium ions in the urine from the DP-resin; (e) directing the flow of aqueous nitric acid containing the strontium ions eluting from the DP-resin through a preconditioned strontium extraction resin (SE-resin) comprising a substituted 18-crown-6 crown ether adsorbed onto a porous polymeric support, to concentrate the strontium ions on the SE-resin; (f) subsequently passing a flow of an aqueous stripping eluent through the SE-resin to elute the strontium ions from the resin, wherein the aqueous stripping eluent comprises water or a dilute acid solution of less that about 0.1 M acid concentration, and has a volume (e.g., about 2 to 5 column volumes) sufficient to elute at least about 85 mole percent (preferably at least about 90, 95, 98 or 99 mole percent) of the strontium ions from the SE-resin; and (g) collecting the flow of aqueous stripping eluent containing the strontium ions eluting from the SE-resin.

The DP-resin is preconditioned with aqueous MSA having a concentration about equal to the concentration of the flow of MSA used to elute the DP-resin in step (c), and the SE-resin is preconditioned with aqueous nitric acid having a concentration about equal to the concentration of the flow of nitric acid used in step (d).

Preferably, the method further comprises the steps of (h) determining the total amount of strontium collected in step (g); and (i) calculating the concentration of strontium in the urine from the amount of strontium determined in step (h) and the known quantity of the urine loaded onto the DP-resin. The total amount of strontium collected can be quantitatively determined by any suitable method, e.g., by scintillation counting for $^{90}$Sr. The concentration of strontium ions in the urine can then be readily calculated from the known quantity of the urine loaded onto the DP-resin and the determined amount of strontium extracted from the urine.

As noted previously, the quantitative determination of $^{90}$Sr ions in urine is difficult due to materials (e.g., bile pigments) that interfere with scintillation, other ions present in the urine matrix, and the low levels of strontium typically present. The organic materials and pigments interfere with scintillation counting by quenching the light emission from the scintillation cocktails used to convert beta-emission energy to visible light. The present method addresses this problem by pretreating the urine as described herein.

Because of the low $^{90}$Sr levels that might typically be expected in urine from subjects exposed to fallout, it is desirable to concentrate the strontium prior to quantitative determination. Attempts to concentrate strontium from urine using single a strontium extraction chromatographic resin are hampered by the other ionic components of urine, particularly alkali metal ions, which are present in much higher concentrations than (40 to 100 mM) than strontium (typically less than 10 pM). For example, a commercially available Sr-extraction chromatographic resin from Eichrom Technologies (referred to as "Sr Resin") cannot effectively concentrate strontium ions from urine to levels suitable for scintillation techniques due the interfering effects of the alkali metal ions. The methods of the present invention address this problem by utilizing a diphosphonic acid-based resin to remove the bulk of the interfering alkali metal ions prior to concentrating the strontium ions on the strontium extraction resin. The strontium obtained in the stripping eluent in the methods of the present invention is surprisingly concentrated by 50-fold or more and is free from scintillation-interfering materials (e.g., pigments), thus greatly improving the accuracy of quantitative determination of $^{90}$Sr by scintillation. In addition, the present methods are unexpectedly rapid. The conventional method of alkaline precipitation, ashing, dissolution, and separations takes approximately 1 day per sample. With the methods and apparatus of the present invention, large samples (e.g., 1 L) can be processed for counting in approximately 3 hours, smaller samples (e.g., 25 mL) can be processed in about 60 minutes, while very small samples (e.g., 5 mL, typical of those gathered from children in triage) can be processed in about 10 minutes.

Unless otherwise specified, concentrations referred to herein are in units of moles per liter, also known as molar concentrations, and abbreviated M, or in some cases in units of millimoles per liter, abbreviated mM. The term "stripping" as used herein with respect to the methods of the present invention, refers to eluting previously retained ions (e.g., strontium ions) from an ion-exchange resin. The term "diphosphonic acid" as used herein refers to functional group on a polymeric resin that comprises two phosphonic acid groups (PO$_3$H$_2$) on a single carbon atom in the resin. The diphosphonic acid resins of the present invention include multiple repeats of such diphosphoic acid groups along the polymeric chains of the resin. As used herein, the term "column volume" refers to the nominal internal volume of the column holding the ion-exchanges resin.

Another aspect of the present invention is an apparatus for extracting strontium ions from a urine sample. The apparatus comprises (a) a first column defining a first chamber therewithin and comprising an inlet at one end of the first chamber, an outlet at the other end of the first chamber, and containing a DP-resin within the first chamber; (b) a second column defining a second chamber therewithin and comprising an inlet at one end of the second chamber, an outlet at the other end of the second chamber, and containing a SE-resin within the second chamber; and (c) a valve mounted between the outlet of the first chamber and the inlet of the second chamber, and comprising a first auxiliary port and a second auxiliary port, which are adapted for fluid-flow connection to the first and second columns, respectively. The valve is adapted for placing the first chamber in fluid-flow communication with the second chamber when the valve is in a flow-through configuration. The valve also is adapted to place the first chamber in fluid-flow communication with the first auxiliary port and to place the second chamber in fluid-flow communication with the second auxiliary port when the valve is in a by-pass configuration. The second chamber preferably has a column volume that is about 10 percent of the column volume of the first chamber.

The apparatus can be utilized in a method of extracting strontium ions from urine e.g., to determine the strontium concentration in the urine. The method comprises the steps of (a) pretreating the urine by acidifying the urine to a pH of less than about 2 with MSA, and removing scintillation-interfering materials from the urine (e.g., by agitating the acidified urine with activated carbon, and separating the activated carbon from the urine); (b) preconditioning the DP-resin of the apparatus with about 0.01 to 2 M aqueous MSA; (c) preconditioning the SE-resin with about 1 to about 10 M nitric acid; (d) loading a known quantity (e.g., about 10 to 30 column volumes) of the decolorized urine onto the preconditioned DP-resin through the inlet of the first chamber; (e) introducing (e.g., through the inlet of the first chamber) a flow of about 0.01 to 2 M aqueous MSA through the first chamber with the valve in the by-pass configuration, wherein the flow of aqueous MSA has a volume (e.g., about 10 to 30 column volumes) sufficient to reduce the concentration of alkali metal ions from the urine eluting off of the DP-resin to about 10 mM or less; (f) subsequently passing a flow of about 1 to 10 M aqueous nitric acid through the first and second chambers with the valve in the flow-through configuration, wherein the flow of aqueous nitric acid has a volume (e.g., about 2 to 5 column volumes) sufficient to elute at least about 85 mole percent (preferably at least about 90, 95, 98 or 99 mole percent) of any strontium ions in the urine from the DP-resin and onto the SE-resin; (g) repositioning the valve in the by-pass configuration and stripping the SE-resin with a flow of an aqueous stripping eluent (e.g., water or a dilute acid solution having an acid concentration of about 0.1 M or less) having a volume (e.g., about 2 to 5 column volumes) sufficient to elute at least about 85 mole percent (preferably at least about 90, 95, 98 or 99 mole percent) of the strontium ions from the SE-resin and though the outlet of the second chamber; and (h) collecting the aqueous stripping eluent containing the strontium ions eluting from the outlet of the second chamber. Steps (a) and (b) can be performed in any order prior to step (d), including simultaneously, if desired. Step (c) can be performed any time prior to step (f).

Preferably, the method further comprises the steps of (i) determining the total amount of strontium collected in step (h); and (j) calculating the concentration of strontium in the urine from the amount of strontium determined in step (i) and the known quantity of the urine loaded onto the DP-resin. As described above, the concentration of strontium in the urine can be readily calculated by determining the total amount the strontium collected (e.g., by scintillation) and calculating the concentration of strontium in the urine from the total amount of strontium collected and the known quantity of urine loaded on the DP-resin.

In another aspect, the present invention provides a rapid and convenient method for pretreating urine to remove from the urine materials that interfere with scintillation. The pretreatment method comprises (a) acidifying the urine to a pH of less than about 2 with MSA (e.g., 0.1 M to 2 M in water), (b) agitating the acidified urine with activated carbon, (e.g., carbon black, activated charcoal, etc.), and then (c) removing the activated carbon from the urine (e.g., by centrifugation, filtration, or a combination thereof). The pretreated urine is surprisingly free from scintillation quenching organic compounds/pigments, making such urine suitable for scintillation analyses, (e.g., tritium or $^{90}Sr$ analysis). Preferably, approximately 1 to 5 wt % of activated carbon (based on urine weight) is used in step (b). Preferably, the urine is agitated with the activated carbon for at least about 1 minute, more preferably about 3 to about 5 minutes.

In some embodiments, the activated carbon is removed by filtration through a suitable filter (e.g., a microporous filter). The filter can be a single-use filter (e.g., disposable filter), or in some embodiments, the filter can be cleaned and reused, for example by back-flushing the filter surface to remove retained carbon and other contaminating materials between uses. Id desired, the back-flushing/cleaning process can be performed using an in-line filter prior to the first ion-exchange column, such that a slurry of acidified urine and activated carbon is directly applied to the apparatus through the filter. The carbon and other contaminants remaining on the filter can then be flushed off in situ. For example a by-pass valve can be positioned between the first column and the filter to allow back-flushing of the filter in isolation from the column. Such back-flushing can even be automated, e.g., for use in combination with an autoinjector to sequentially apply different urine samples to the column when performing multiple analyses. For automated handling of multiple samples, the column conditioning steps and eluent collection step preferably would be automated, as well, e.g., by use of automated valves and sample collecting devices, which are well known in the chromatographic field. A computer interface with process control software can be used to control and direct such automated systems, if desired.

In the methods of the present invention, the pretreatment of raw urine samples (e.g., by acidification with MSA and stirring with activated carbon) removes the colored interferences and most other quenching agents from urine within several minutes. The potentially interfering radioactive and non-radioactive ions (e.g., alkaline earths and alkali metals) are eliminated first by the DP-resin column, and then by the SE-resin column (e.g., $^{90}Y$ and any remaining alkali and alkaline earth metal ions) resulting in purified and concentrated $^{90}Sr$ in the final eluate that is directly suitable for liquid scintillation counting. The serial use of an ion-exchange resin column and a strontium extraction chromatographic resin column, along with simple mixing and filter operations, makes the methods of the present invention amendable to automation. Because the colored organic quenching materials are removed from the urine prior to loading onto the DP-resin ion-exchange column, the columns of DP-resin and SE-resin do not foul after multiple uses. This is an explicit requirement of the CDC for any acceptable strontium analysis method. The present methods and apparatus can rapidly and efficiently separate strontium ions from urine in accordance with the current CDC guidelines.

BRIEF DESCRIPTION OF THE DRAWINGS

The invention comprises or consists of certain novel features and a combination of parts hereinafter fully described, illustrated in the accompanying drawings, it being understood that various changes in the details may be made without departing from the spirit, or sacrificing any of the advantages of the present invention.

DETAILED DESCRIPTION OF THE PREFERRED EMBODIMENTS

Figure 1:
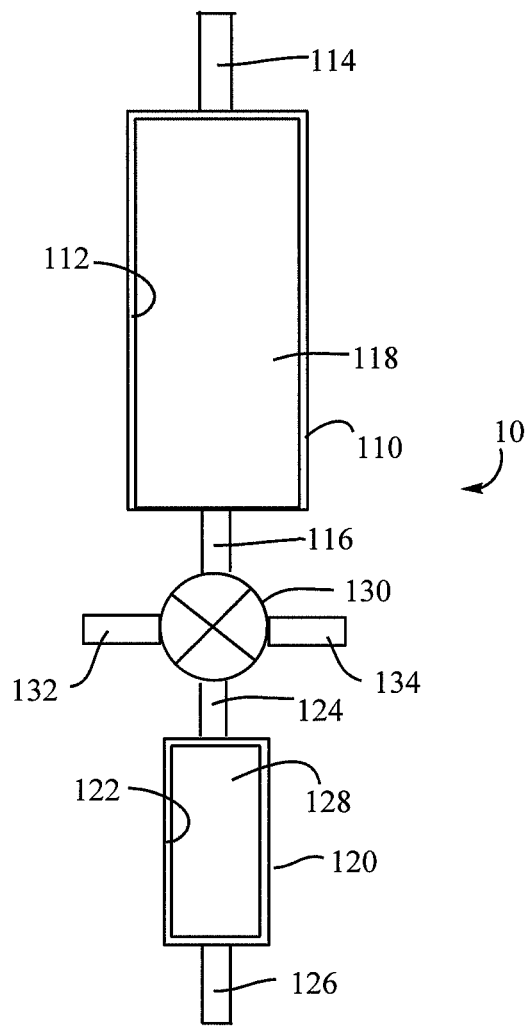
FIG. 1 depicts a schematic cross-section of an apparatus of the present invention.

This invention relates to methods of rapidly and efficiently extracting strontium, particularly $^{90}Sr$, from urine (e.g., human urine). In the methods and apparatus of the present invention an ion-exchange resin and a strontium extraction chromatographic resin are utilized in tandem to efficiently separate strontium ions from urine. The ion-exchange resin is a diphosphonic acid-based resin (DP-resin) comprising diphosphonic acid groups and sulfonic acid groups bound to a particulate polymeric matrix. The strontium extraction resin (SE-resin) comprises a substituted 18-crown-6 crown ether, e.g., 18-crown-6 substituted with one or more cyclic alkyl groups (for example, one or more cyclohexyl groups or alkyl-substituted cyclohexyl groups fused to the crown ether ring), adsorbed on an inert porous polymeric support.

Ion-exchange resins suitable for use as the DP-resin include those described in U.S. Pat. No. 5,281,631, which is incorporated herein by reference in it is entirety. A particularly useful DP-resin in the apparatus and methods of the present invention is the DIPHONIX® resin, which is commercially available from Eichrom Technologies LLC (Lisle, Ill.), and which is described by the manufacturer as a gel-type cation resin comprising a polystyrene/divinylbenzene matrix with phosphonic acid and sulfonic acid groups bound to the matrix. The phosphonic acid groups are arrayed in pairs with two phosphonic acid groups on a single carbon, forming a diphosphonic acid group. The DIPHONIX® resin is provided in bead form (approximately spherical beads). DIPHONIX® resin reportedly comprises a polymer of Formula (I):

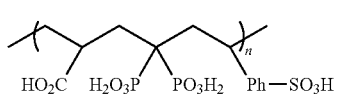

(I)

in which "n" is a number of sufficient size to afford a water-insoluble material (e.g., greater than 1000) and in which two phosphonic acid groups are present on a single carbon atom forming a diphosphonic acid group.

A particularly useful SE-resin in the apparatus and methods of the present invention is sold under the trade name "Sr Resin" by Eichrom Technologies LLC (Lisle, Ill.). Sr Resin is described by the manufacturer as comprising about 1 M 4,4' (5')-di-tert-butylcyclohexano 18-crown-6 in 1-octanol, adsorbed onto an inert porous polymeric support (a polyacrylate resin). The bed-density of the Sr resin reportedly is about 0.35 g/mL. The maximum capacity for $Sr^{2+}$ for Sr Resin reportedly is about 21 mg per 2 mL of column volume. The working Sr capacity recommended by the manufacturer for the Sr Resin reportedly is about 10 to 20% of the maximum capacity. Since the crown ether component of Sr Resin has affinity for potassium and sodium ions, addition of >10 mM $K^+$ or >100 mM $Na^+$ considerably reduces the retention of $Sr^{2+}$. Urine samples typically comprise 100-150 mM $Na^+$ and 50-100 mM $K^+$, thus the retention of $Sr^{2+}$ in such saline solutions is greatly reduced.

The structural formula for crown ether component of Sr Resin is provided in Formula (II):

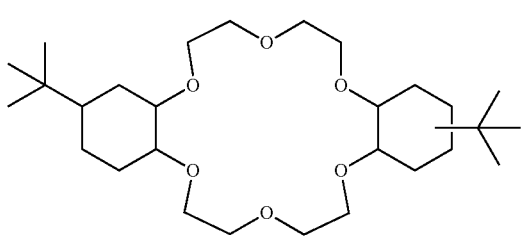

(II)

in which the tert-butyl group of the cyclohexanyl ring on the right in the structure as illustrated can be on the 4' or 5' position.

In the methods of the present invention, the total amount of strontium ions extracted from the urine can be quantitatively determined by any suitable method. Preferably, in the case of radioactive $^{90}Sr$, the quantity of strontium ions is determined by measuring the radioactivity of the collected eluent (e.g., by scintillation) and the total volume of eluent collected, and then calculating the quantity of $^{90}Sr^{2+}$ in the urine that was loaded onto the DP-resin from those measured quantities. The concentration of $^{90}Sr^{2+}$ in the urine is then readily calculated from the known quantity of urine loaded onto the DP-resin and the amount of $^{90}Sr^{2+}$ extracted from the urine. Alternatively, the amount of $^{90}Sr^{2+}$ in the stripping eluent can be determined by differential counting after evaporating the eluent away, by Geiger-Mueller counting, by a silica-based detector, or any other suitable method, as is well known in the art.

Figure 2:
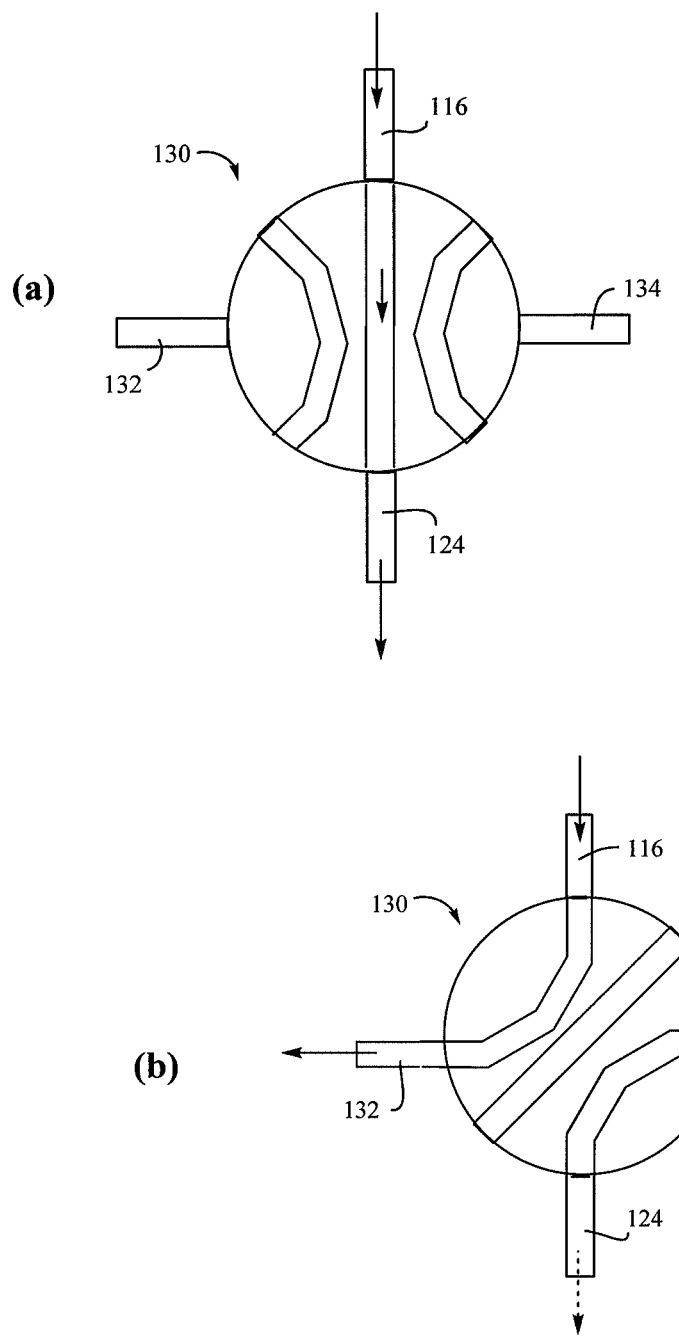
FIG. 2 schematically depicts the valve component of the apparatus shown in FIG. 1; Panel (a) depicts the valve in the flow-through configuration; and Panel (b) depicts the valve in the by-pass configuration.

A schematic cross-sectional representation of an apparatus of the present invention is shown in FIG. 1. Apparatus 10 comprises first column 110 defining first chamber 112 therewithin. Inlet 114 and outlet 116 open into first chamber 112 Particulate DP-resin 118 fills first chamber 112. Second column 120 defines second chamber 122 therewithin. Particulate SE-resin 128 fills second chamber 122. Inlet 124 and outlet 126 open into second chamber 126. Outlet 116 of first chamber 112 is adapted for fluid-flow connection to inlet 124 of second chamber 122 by valve 130, which is connectable with auxiliary ports 132 and 134. Valve 130 can be positioned in a pass-through configuration, as shown in FIG. 2, Panel (a), to connect outlet 116 with inlet 124. Valve 130 also can be positioned in a by-pass configuration, as shown in FIG. 2, Panel (b), such that outlet 116 is open to port 132 for passing fluid through first chamber 112 without connecting to second chamber 122; and inlet 124 is open to port 134 for passing fluid through second chamber 122 without passing through first chamber 112.

During operation, a decolorized urine sample as described herein is loaded onto DP-resin 118 via inlet 114. After the urine is loaded onto resin 118, a solution of MSA (about 0.01 to 2 M, preferably about 0.1 to 0.22 M) is eluted through the first chamber 112, with valve 130 positioned in the by-pass configuration (FIG. 2b, solid and dashed arrows show flow pathway of eluent through the valve). MSA solution eluting out of port 132 can be collected and/or discarded. After a sufficient volume of MSA has been eluted through first chamber 112 to remove at least a portion of the alkali mental ions and organic components of the urine (typically about 10 to about 30 column volumes), valve 130 is repositioned in the flow-through configuration (FIG. 2a, arrows show fluid pathway through the valve) and a nitric acid solution (about 2 to 5 column volumes of 1 to 10 M nitric acid) is passed through first chamber 112 and second chamber 122 to elute the strontium from DP-resin 118 onto SE-resin 128. Valve 130 is then placed back into the by-pass configuration and an aqueous stripping eluent (e.g., about 2 to 5 column volumes of deionized water or preferably dilute nitric acid) is passed through port 134 and into second chamber 122 to elute the strontium ions off SE-resin 128 and out through outlet 126. The stripping eluent containing strontium ions eluting from outlet 126 is then collected and the strontium content thereof can be determined as discussed herein.

The typical volumes of the two columns are 2 mL for the DP-resin column and 200 μL for the SE-resin column. For a 20 mL load of urine (preferably pre-treated with acid and activated carbon), the DP-resin column can concentrate Sr by a factor of about 2.5 to 3.5 and the SE-resin column by a factor of about 20, resulting in an overall concentration factor >50.

The DP-resins and SE-resins, as described herein exhibit opposite trends in the dependence of the corresponding distribution ratios for $Sr^{2+}$ ($D_{Sr}$, which is the ratio of concentrations of the ions in the solid and liquid phases) as a function of the acidity of the carrier phase. This property allows one to use these two columns in tandem, as the high acidity that facilitates stripping of $^{90}Sr$ from the DP-resin is optimum for loading strontium onto the SE-resin, and vice versa. Aqueous MSA solutions were selected as the carrier phase for the initial elution through the DP-resin, because the presence of this acid (in <4 M concentrations) has no effect on $^{90}$Sr uptake by the SE-resin, while for the DP-resin, only the overall acidity (hydronium ion concentration) determines $D_{Sr}$ (i.e., the same concentrations of the nitric acid and MSA have about the same effect on ion retention). Since nitric acid tends to nitrate aromatic constituents in urine, resulting in strong coloration (even when these components are present at low concentration), the contact with strong (e.g., 1 to 10 M) nitric acid preferably is delayed until the most of the residual organic components have been eluted away (e.g., along with the alkali metal ions). In the present invention, the DP-resin is used to reduce the concentration of $K^+$ and $Na^+$ ions below about 10 mM, which reduces interference enough to utilize a minimal-volume (e.g., about 10% of the column volume of the DP-resin) SE-resin column to concentrate and decontaminate the strontium-90.

As is well known in the art, the retention of a given ion on an ion-exchange chromatographic column, having an infinite number of theoretical plates, and operating under quasi-equilibrium conditions, is characterized by the constant $k_{ex}$, corresponding to the elution volume (in column volumes) required for the peak concentration (for a small loaded sample) to reach the opposite end of the column during the elution. The same $k_{ex}$ value gives the approximate load volume under which such a column would not break through for a given ion. While actual ion-exchange columns have a finite number of theoretical plates and the conditions may not correspond to quasi-equilibrium, $k_{ex}$ still is a convenient parameter for characterizing column operation. The coefficient $k_{ex}$ is related to the weight distribution coefficient $D_w$ through Equation (1):

$$k_{ex}=D_w \rho V_s/V_m, \quad (1)$$

where $\rho$ is the density of the resin, $V_s$ is the volume of the stationary phase, $V_m$ is the volume of the mobile phase, and $V_s/(V_s+V_m)$ is the bed ratio. Using $\rho=1.16$ g/mL and a bed ratio of 30% for the DP-resin yields $k_{ex}$ of about $D_w/2.01$. The retention coefficients $k_{ex}$ for $Sr^{2+}$, $K^+$, and $Na^+$ with the commercial DP-resin, DIPHONIX® resin, is calculated by substituting the data on the resin provided by the manufacturer into Eq. 1. Calculated $k_{ex}$ values are plotted as a function of the acidity of the mobile phase (the MSA concentration) in FIG. 3. Referencing the latter concentration to standard conditions (selected as 0.1 M MSA) for the aqueous solution yields Equation (2):

$$k_{ex}/k_{ex}^\circ \approx Q^\beta, \quad (2)$$

where $Q=[MSA]_o/[MSA]$. For the DIPHONIX® resin, the coefficient $\beta$ is close to the nominal charge for the eluted ion: i.e., for $Sr^{2+}$, $\beta$ is about 1.93±0.07, and for $Na^+$, $\beta$ is about 0.99±0.03. In the presence of a high salt concentrations, $k_{ex}$ decreases, but Eq. (2) still holds approximately, albeit for reduced $\beta$ (see FIG. 4). As shown in FIG. 5, this decrease is significant, but the shape of the dependencies for $k_{ex}$ vs. the concentration of the salts added does not depend on the bed ratio. The decrease with the ionic strength of the solution can be described from the empirical Equation (3):

$$k_{ex}/k_{ex}^\circ \approx Q^\beta/(1+[Q[C]/[C]_o]^v), \quad (3)$$

where [C] is the concentration of the metal ions (separately). For $Sr^{2+}$, $[C]_o$ is about 19.5 mM and v is about 1.25; for $Na^+$, $[C]_o$ is about 55 mM and v is about 1.

Figure 4:
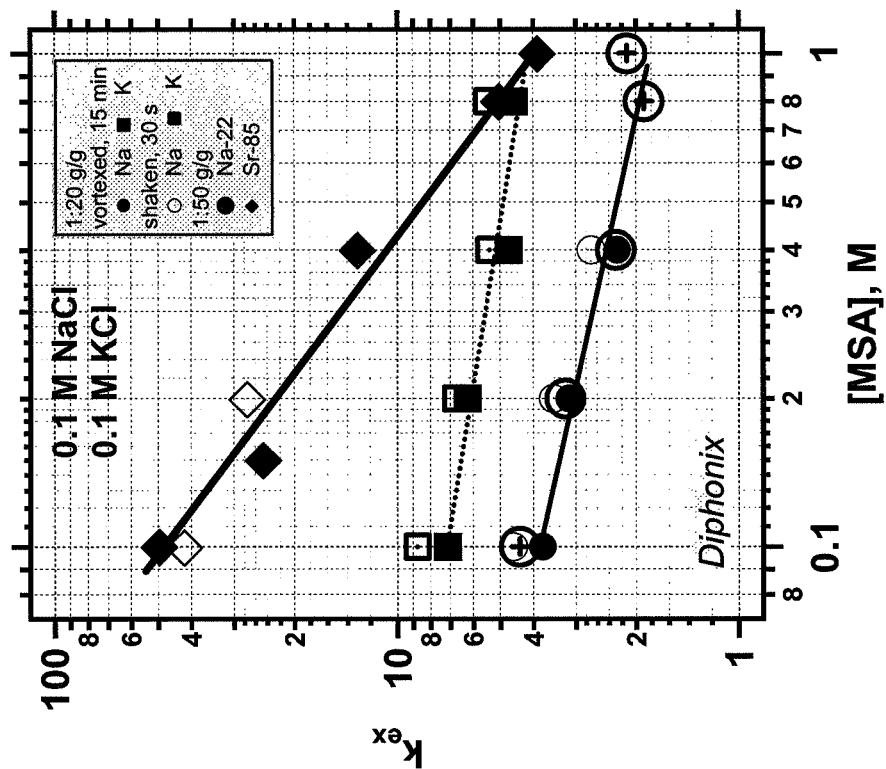
FIG. 4 provides a graph of $k_{ex}$ values for Na, K, and Sr ions versus MSA concentration for a DIPHONIX® resin column with 100 mM alkali metal ion concentrations (a simulated urine solution) obtained using $^{22}Na^+$ and $^{85}Sr^{2+}$ as tracers; data were determined in the same manner as in FIG. 3, except for an aqueous solution containing 0.1 M NaCl and 0.1 M KCl ("simulated urine matrix") was used; the distribution coefficients for K and Na were obtained after either agitating the solution for about 0.5 min on an orbital shaker or 15 min of vigorous vortexing.
Figure 3:
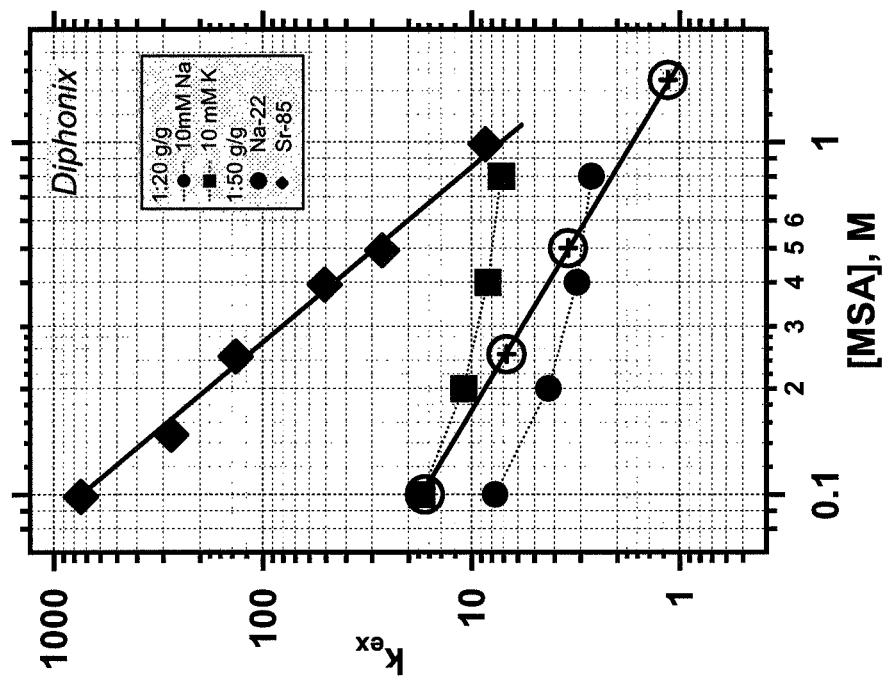
FIG. 3 provides a graph of $k_{ex}$ values for Na, K, and Sr ions versus MSA concentration for a DIPHONIX® resin column with 10 mM alkali metal ion concentrations, obtained using $^{22}Na^+$ and $^{85}Sr^{2+}$ as tracers; data derived by assuming a 0.3 bed ratio and using data for distribution coefficients obtained from the manufacturer; for sodium, data were obtained using $^{22}Na$ tracer and inductively coupled plasma optical emission spectroscopy (for 10 mM alkali); the mass ratio for (wet) resin to aqueous solution is indicated in the plot.
Figure 6:
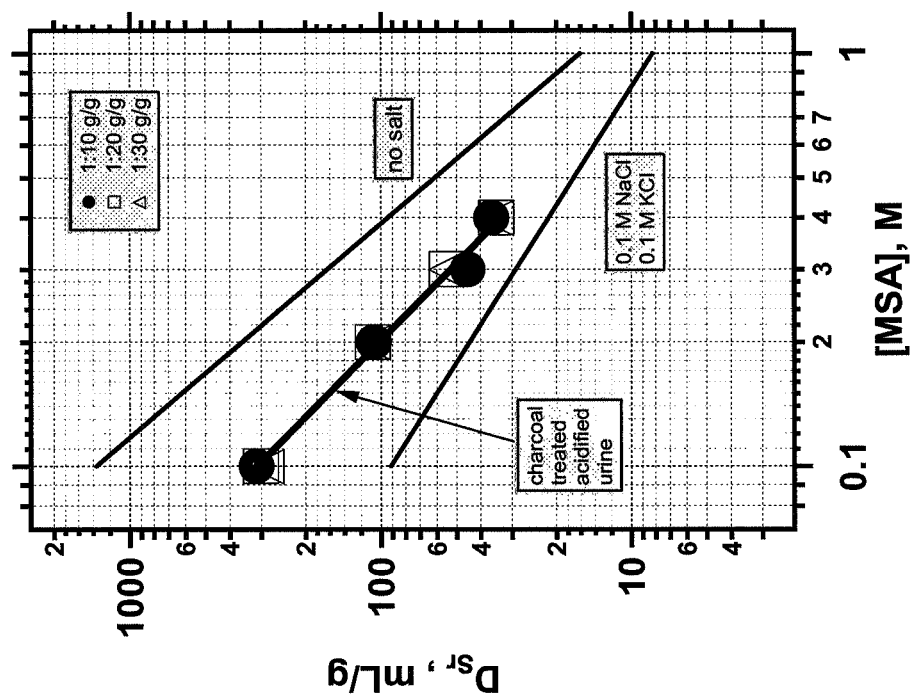
FIG. 6 provides a graph of distribution ratio ($D_{Sr}$) values versus MSA concentration for a DIPHONIX® resin column; acid dependence of distribution ratio for strontium-85 on DIPHONIX® resin for urine matrix (symbols), aqueous solution (gray line), and 0.1 M NaCl+0.1 M KCl solution (black line); the distribution coefficients remained constant for 1:10 to 1:30 g/g mass ratio of the wet resin to the liquid sample.
Figure 5:
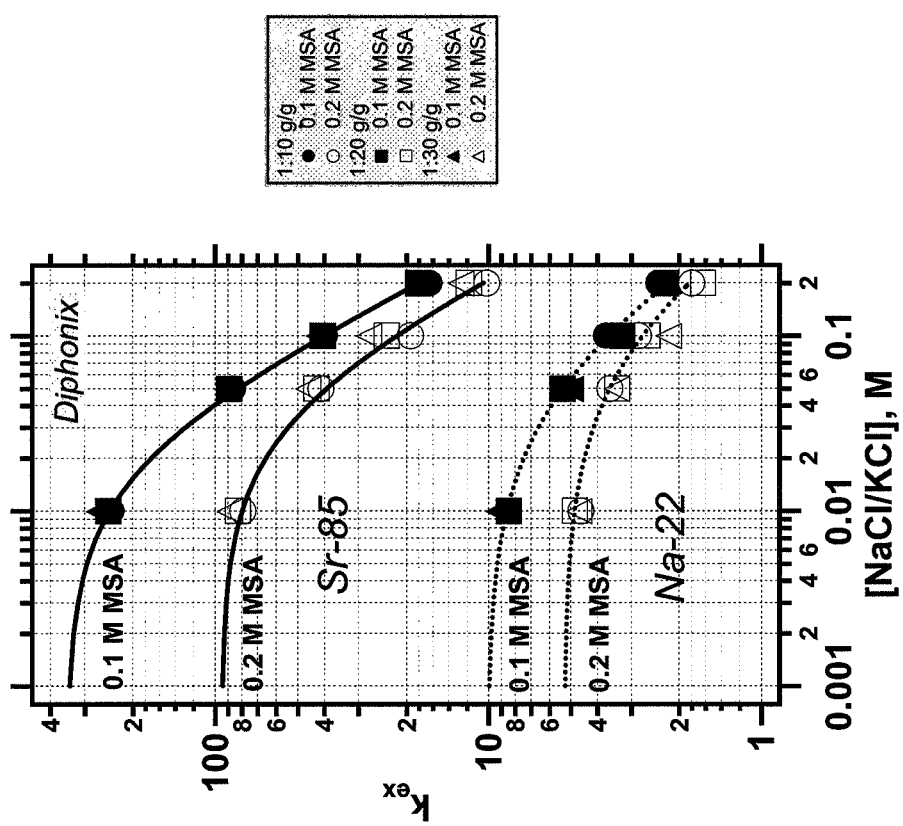
FIG. 5 provides a graph of $k_{ex}$ values for Na, K, and Sr ions versus molar concentration of alkali metal ions for a DIPHONIX® resin column eluted with 0.1 M and 0.2 M MSA obtained using $^{22}Na^+$ and $^{85}Sr^{2+}$ as tracers; lines are fitted based on the equations described herein; data show dependence of $k_{ex}$ for $^{85}Sr$ and $^{22}Na$ extraction with DIPHONIX® resin as a function of the molar concentration of sodium/potassium (1:1) ions in 0.1 M and 0.2 M MSA solutions; the lines are fits to equation given in the text.
Figure 8:
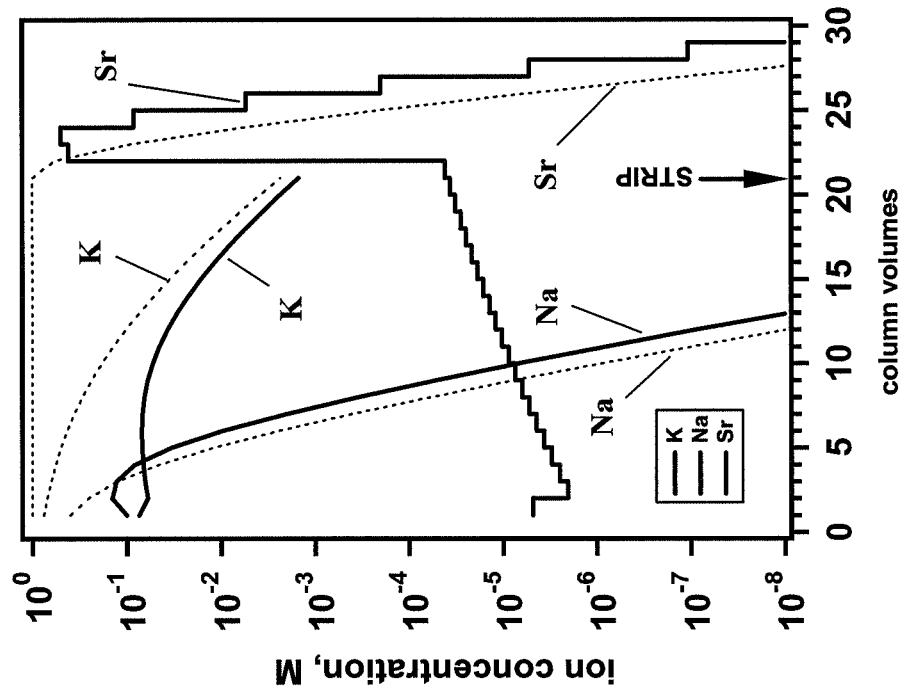
FIG. 8 provides a graph of calculated molar (M) ion concentrations for K, Na, and Sr ions versus column volumes of elution calculated based in the parameters in Table 1 and simulation conditions for example No. 2 in Table 2; 10 plate column, 10 col. vol. load, 20 col. vol. elution (0.2 M MSA), 4 col. vol. strip (3 M nitric acid).
Figure 7:
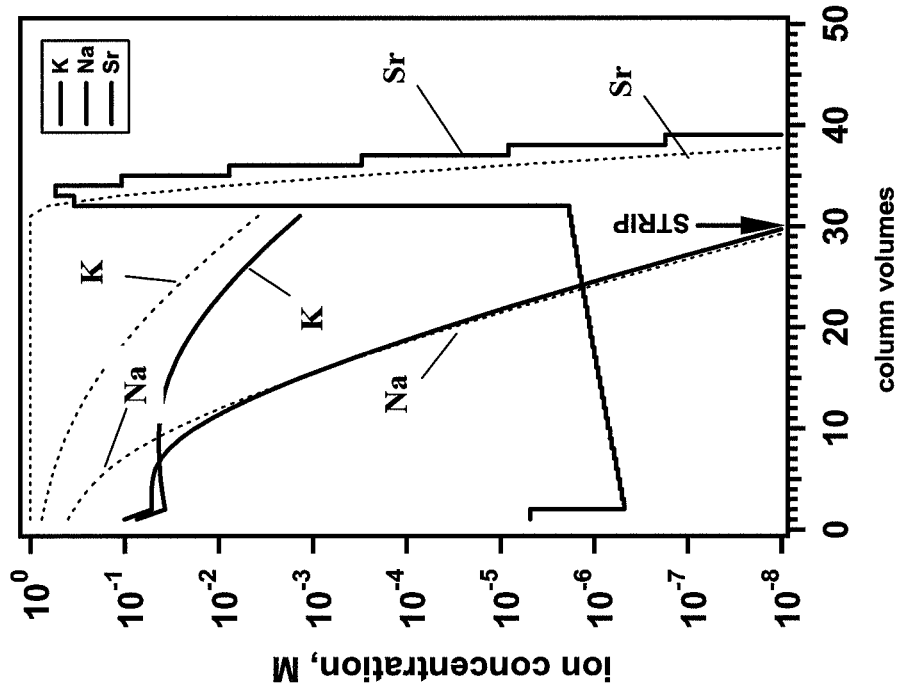
FIG. 7 provides a graph of calculated molar (M) ion concentrations for K, Na, and Sr ions versus column volumes of elution calculated based in the parameters in Table 1 and simulation conditions for example No. 1 in Table 2; solid lines are concentrations in the eluent, and dashed lines are the average concentrations on the column (both phases); 10 plate column, 10 col. vol. load, 30 col. vol. elution (0.1 M MSA), 4 col. vol. strip (3 M nitric acid).
Figure 10:
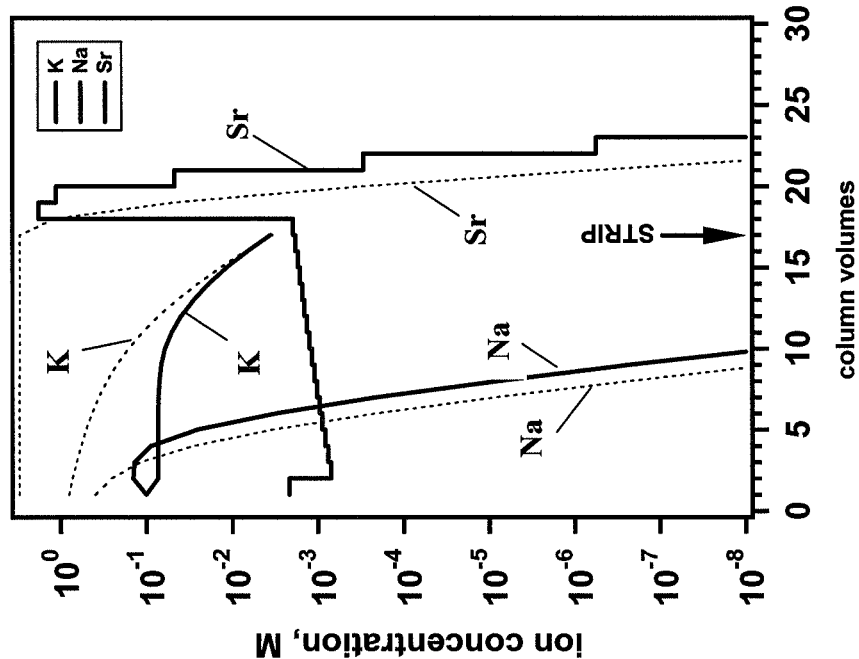
FIG. 10 provides a graph of calculated molar (M) ion concentrations for K, Na, and Sr ions versus column volumes of elution calculated based in the parameters in Table 1 and simulation conditions for example No. 4 in Table 2; 20 plate column, 30 col. vol. load, 16 col. vol. elution (0.2 M MSA), 4 col. vol. strip (3 M nitric acid).
Figure 9:
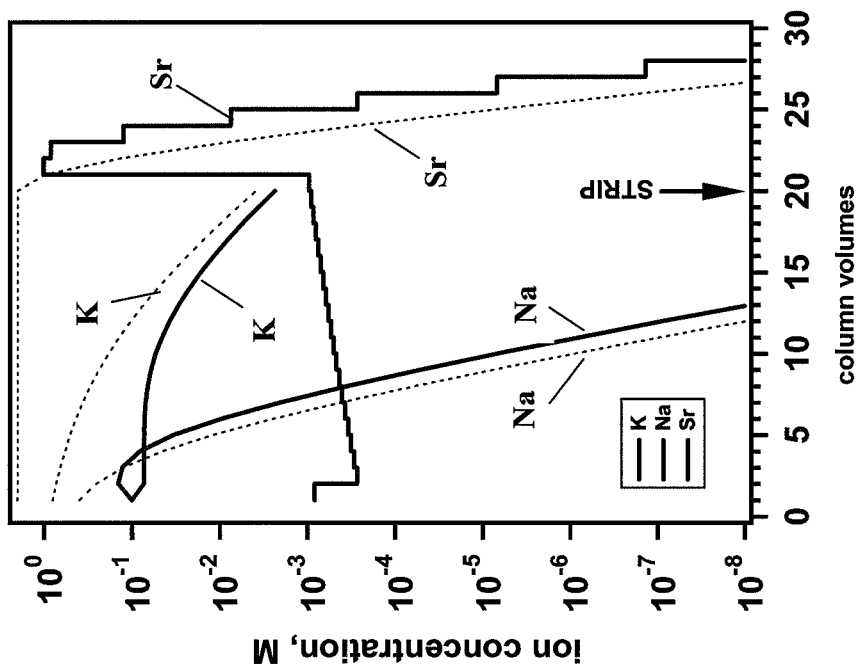
FIG. 9 provides a graph of calculated molar (M) ion concentrations for K, Na, and Sr ions versus column volumes of elution calculated based in the parameters in Table 1 and simulation conditions for example No. 3 in Table 2; 10 plate column, 20 col. vol. load, 19 col. vol. elution (0.2 M MSA), 4 col. vol. strip (3 M nitric acid).

A closer look at FIG. 4 and FIG. 5 reveals that, at 0.1 M MSA with the "simulated urine" saline solution containing 0.1 M sodium and potassium chloride, $k_{ex}$ is approximately 40 for $Sr^{2+}$ and about 5 and about 8 for sodium and potassium, respectively. From these data one can calculate that up to about 30 column volumes can be loaded on a column with a large (e.g., >20) number of theoretical plates without $Sr^{2+}$ breaking through, while $Na^+$ and $K^+$ break through the column at such a loading. Increasing the acidity over 0.22 M MSA typically is not preferred, because the difference in $k_{ex}$ for $K^+$ and $Sr^{2+}$ becomes smaller as the acidity increases, and the two ions become more difficult to separate on the column. A preferred embodiment of the present invention comprises loading as much urine on the column as is practical without $Sr^{2+}$ breaking through the column, and then eluting the $K^+$ and $Na^+$ with minimal loss of $Sr^{2+}$. As shown in FIG. 3, for elution with 0.1 M MSA, $k_{ex}$ is <20 for $K^+$ and $Na^+$, whereas $k_{ex}$ is >100 for $Sr^{2+}$, so the strontium and the alkali metal ions can be completely separated on a time scale approximately equal to the time required to load the urine sample onto the DP-resin column. As suggested by the information in FIG. 6, the distribution ratios for Sr ion in a human urine sample are intermediate between that of an aqueous solution and a saline solution. The saline solution represents the worst case scenario (abnormally salty urine).

Model Calculations

To simulate the performance of the column, the equations described above were used to calculate equilibria for each plate of a model column comprising serially connected DP-resin and SE-resin columns. The coefficients $k_{ex}$ used in these calculations are provided in Table 1. Four loading/elution scenarios are considered in Table 2, and the simulated elution profiles are provided in FIGS. 7 to 10. For these simulations, the model column was loaded with about 10 to 30 column volumes of 0.1 M NaCl+0.1 M KCl in 0.1 M MSA, and the metal ions were eluted using 15 to 30 volumes of 0.1 or 0.2 M MSA. At the end of the elution, the column was stripped with four column volumes of 3 M nitric acid to remove the strontium ions from the resin. As shown from these plots and Table 2, a 20 column volume elution with MSA is sufficient to reduce the $K^+$ concentration to <2 mM in the stripping eluent, and to collect >99% of the $Sr^{2+}$, which provides a $Sr^2$ concentration factor in the range of about 2.5 to 7.5, depending on the loading. The elution with MSA can be as high as 30 column volumes, provided that the column has >20 theoretical plates. For a 10-plate column, a 10 to 20 column volume load of pre-treated urine can be used.

Results and Discussion of Example Separations

Figure 11:
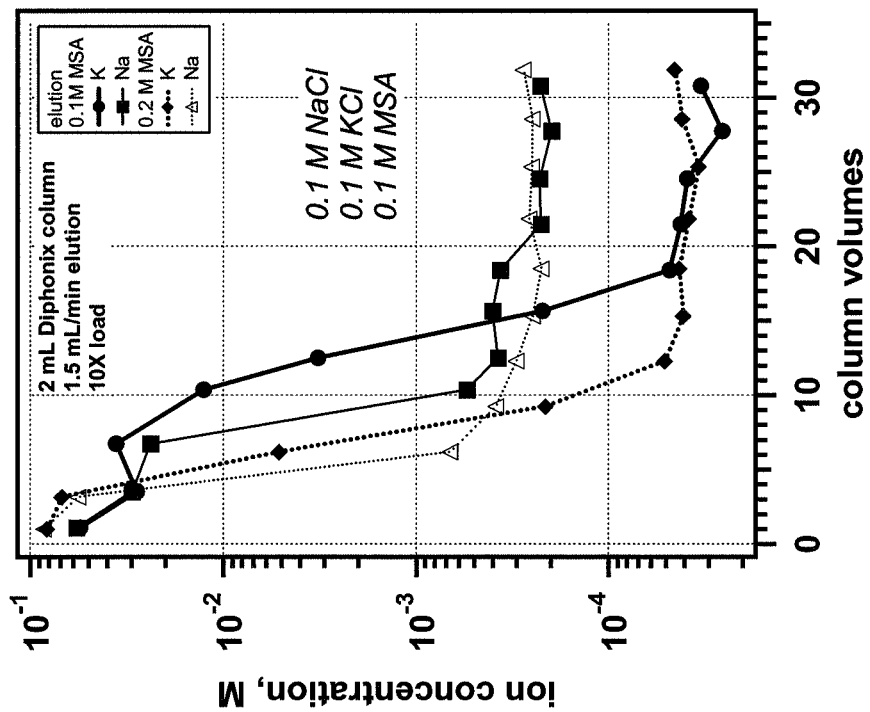
FIG. 11 provides a graph of measured molar (M) ion concentrations for K and Na ions in the eluent versus column volumes of elution for example No. 1 in Table 2; conditions include 10 column volume load of saline solution (0.1 M NaCl+0.1 M KCl) acidified with 0.1 M MSA (2 mL DIPHONIX® resin column, 0.54 cm$^2$×3.7 cm); the elution was either with 0.1 M MSA (solid lines, filled symbols) or 0.2 M MSA (dashed lines, open symbols).

The performance of an actual DP-resin column (i.e., a 2 mL DIPHONIX® resin column) does not quite follow the model performance, since the actual DIPHONIX® resin column operates far from equilibrium. In the simplest evaluation (No. 1 in Table 2), 10 column volumes of the saline solution in 0.1 M MSA were loaded on a 0.54 cm$^2$×3.7 cm (2 mL) column, then the system was eluted at about 1.5 mL/min with 0.1 or 0.2 M MSA. As shown in FIG. 11, the alkali metal ions on the column were eluted down to <1 mM in 20 column volumes (the minimal volumes for elution of each ion are given in Table 3).

Figure 12:
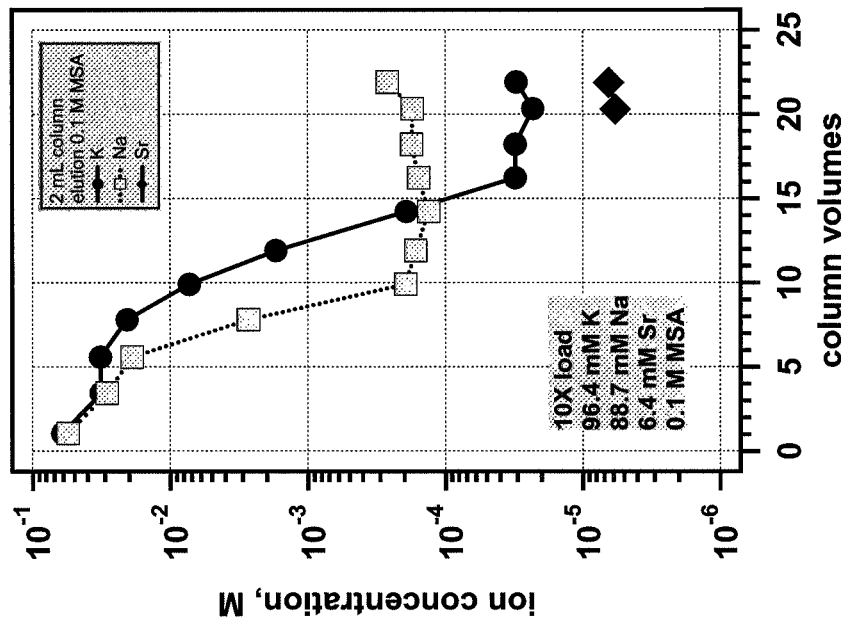
FIG. 12 provides a graph of measured molar (M) ion concentrations for K, Na and Sr ions in the eluent versus column volumes of elution for example No. 2 in Table 2; conditions include 10 column volume load of Sr-spiked saline solution acidified with 0.1 M MSA; ion concentrations in the load are also given in the plot.

As shown in FIG. 12 and Table 4 for evaluation No. 2, stripping the DIPHONIX® resin column with 10 mM nitric acid after elution with 22 column volumes of MSA recovered about 100% of the strontium ion and reduced the concentration of sodium and potassium ions to the limits of detectability. In this evaluation, only <40% of the alkali metal ions were retained on the column during loading, while all strontium ions were retained.

Figure 13:
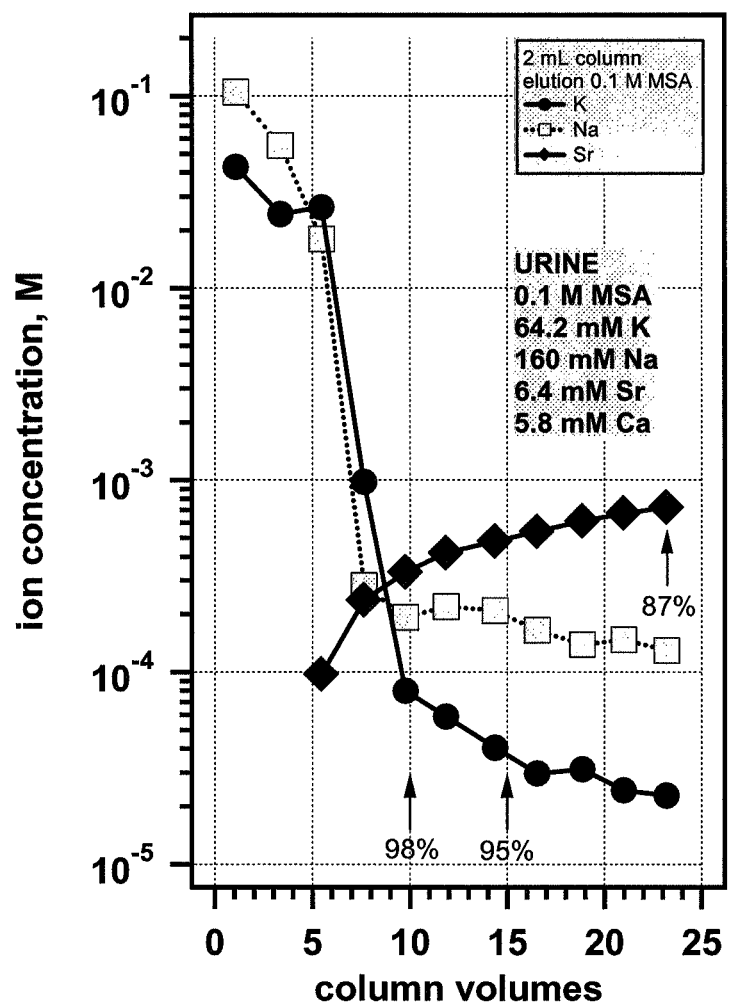
FIG. 13 provides a graph of measured molar (M) ion concentrations for K, Na and Sr ions in the eluent versus column volumes of elution for example No. 3 in Table 4 (human urine spiked with Sr); conditions include 10 column volume load of Sr-spiked human urine acidified with 0.1 M MSA; ion concentrations in the load are also given in the plot.

Evaluation No. 3 was performed with acidified urine (0.1 M MSA) spiked with about 6.5 mM strontium ion (FIG. 13 and Table 4). Less than 30% of the alkali metal ions were retained during 10 column volume loading on the DIPHONIX® resin column. The alkali metal ions were eluted down to negligible concentrations in the 10 column volume elution with 0.1 M MSA, whereas about 98% of strontium ion was retained at the column. A 15 column volume elution resulted in about 5% loss of Sr, while a 22 column volume elution resulted in about 13% loss of strontium. Thus, 87% of the Sr was recovered in the nitric acid elution following this 22 column volume MSA elution. These results suggest that an unidentified component of urine unexpectedly decreases the retention coefficients below those in a saline solution of similar ionic strength, which results in non-equilibrium conditions. Even though the column operated far from equilibrium, the $Sr^{2+}$ and $K^+$ were still well separated, and the strontium was largely decontaminated from the alkali metal cations.

Figure 14:
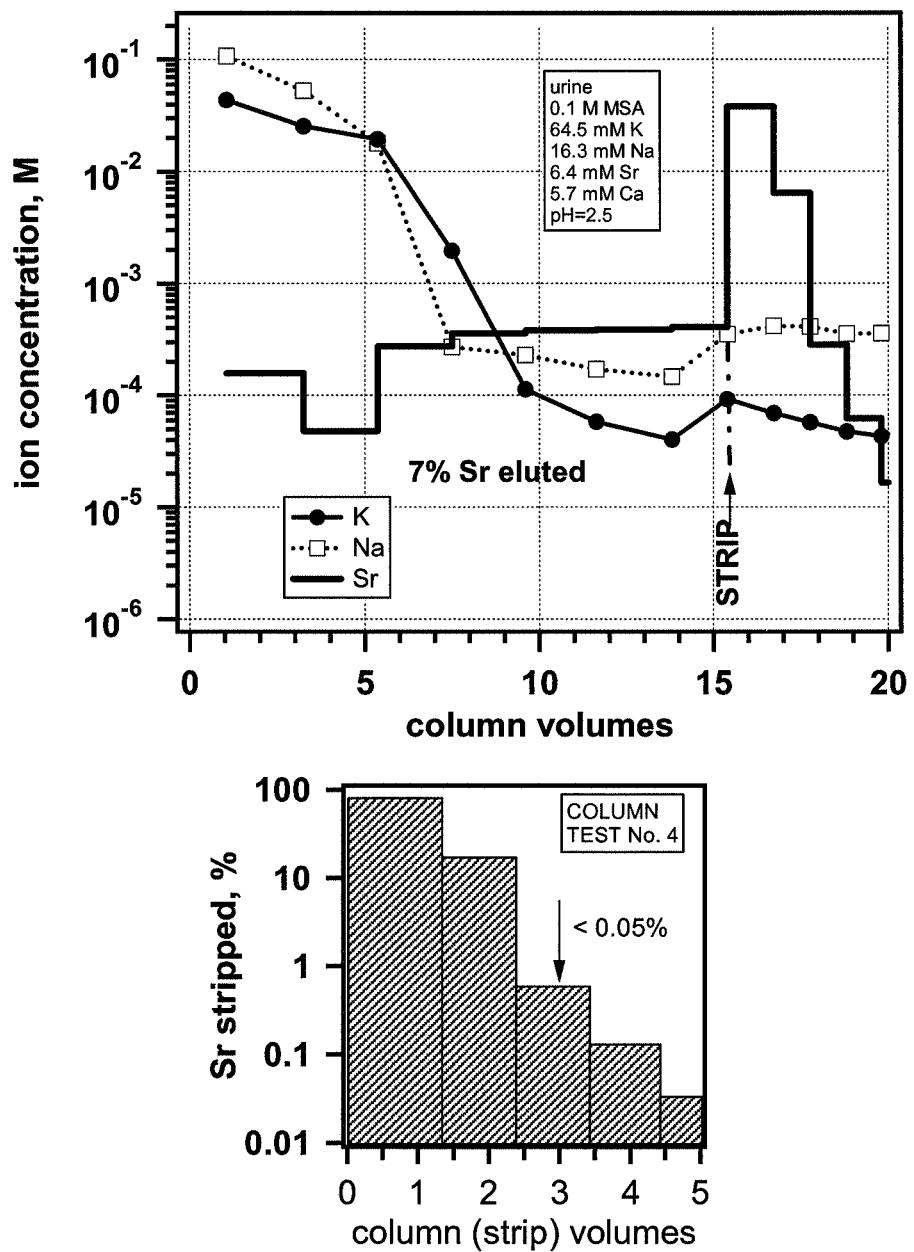
FIG. 14 (top panel) provides a graph of measured molar (M) ion concentrations for K, Na and Sr ions in the eluent versus column volumes of elution for example No. 4 in Table 4 (human urine spiked with Sr); (bottom panel) provides a graph of percentage of Sr stripped from the column versus column volumes of nitric acid eluent; like the example shown in FIG. 12, Sr was stripped after 15 column volumes of 3 M HNO$_3$ was eluted; the loss of Sr$^{2+}$ during this 0.1 M MSA elution was 7%; 3 column volume stripping of the column using 3 M HNO$_3$ removed 99.95% of Sr$^{2+}$ on the column; the concentration factor for strontium was about 3.2; the concentration of K$^+$ and Na$^+$ in the strip solution was <1 mM.

FIG. 14 shows the results of DIPHONIX® resin column evaluation No. 4 for a urine sample (10 column volume loading, as in FIG. 13) after a 15 column volume elution using 0.1 M MSA. Approximately 7% of the Sr was eluted from the DIPHONIX® resin column, so the actual recovery of strontium was about 93%; however, 99.95% of the $Sr^{2+}$ on the DIPHONIX® resin column was stripped with just 3 column volumes of 3 M $HNO_3$. This resulted in about a 3.2× increase in the concentration of $Sr^{2+}$ in the strip eluent. Approximately 82% of $Sr^{2+}$ on the column was eluted with the first column volume of the 3 M nitric acid, generating a very concentrated strontium stream.

Figure 15:
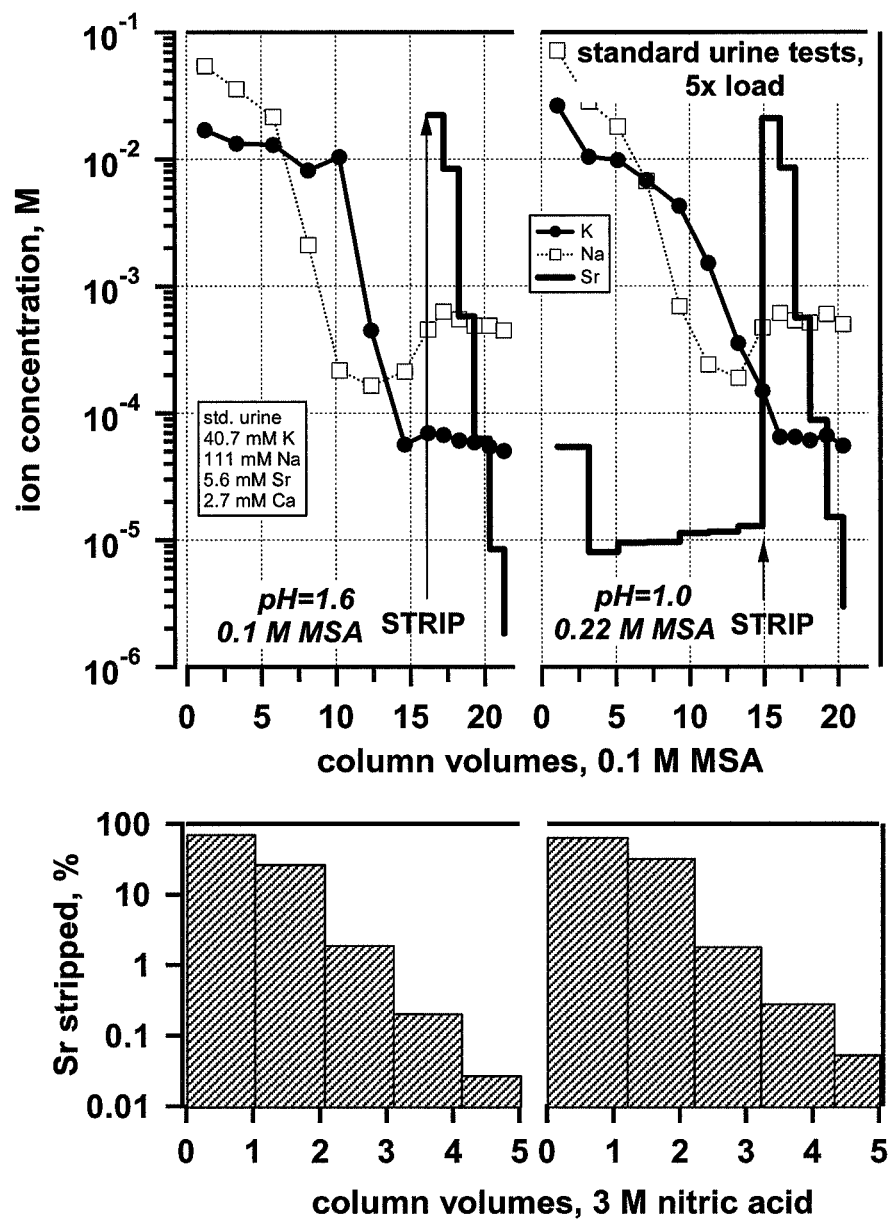
FIG. 15 (top panel) provides a graph of measured molar (M) ion concentrations for K, Na and Sr ions in the eluent versus column volumes of elution for standard urine spiked with Sr at 2 different MSA concentrations; (bottom panel) provides a graph of percentage of Sr stripped from the column versus column volumes of nitric acid eluent; results from evaluation of standardized, frozen "normal human urine" obtained from Innovative Research, Inc. (Lot IR100706); the urine sample was acidified with 0.1 M MSA (pH 1.6) or 0.22 M MSA (pH 1) and then stirred with activated carbon; chromatographic conditions: 5 column volumes of the pre-treated urine were loaded on the 2 mL DIPHONIX® resin column, 15 column volumes of 0.1 M MSA were eluted, and the column was stripped using 3 M HNO$_3$.

FIG. 15 presents results from an evaluation of an apparatus of the present invention using standardized frozen "normal human urine" (Lot IR100706 obtained from Innovative Research, Inc). In this example a 5 column volume sample of treated, acidified urine containing about 5.6 mM $Sr^{2+}$, 111 nM $Na^+$, 40.7 mM $K^+$, and 2.7 mM $Ca^{2+}$, was loaded on a 2 mL DIPHONIX® resin column, which was connected to a 0.2 mL Sr Resin column (Eichrom). In one sample, the urine was acidified to a pH of about 1 using 0.22 M MSA (the urine is buffering); in another sample, 0.1 M MSA was added to achieve a pH of about 1.6. There was no loss of Sr during loading, and <0.1% loss of Sr during the elution with 15 column volumes of MSA, in both cases. Subsequent stripping the column (after elution with 0.1 M MSA) with 3 column volumes of 3 M $HNO_3$ recovered 99.7% of Sr on the column. The concentrations of $K^+$ and $Na^+$ in the strip solution were <0.3 mM (FIG. 15).

Elution with 3 M $HNO_3$ (3 column volumes) corresponds to the conditions under which $k_{ex}$ for strontium on the Sr Resin column is about 60 (see Table 1). Since the volume of the Sr Resin column was about 10% of the volume of DIPHONIX® resin column, loading the nitric acid stripping solution on a 20-plate Sr Resin column corresponds to about 30 column volumes, resulting in a loss of <0.1% Sr during the loading. After 5 more column volumes of nitric acid were eluted through the Sr Resin column to wash away undesirable ions and a 2 column volume stripping solution of 10 mM nitric acid was eluted through the Sr Resin column, $Sr^{2+}$ was concentrated about 20 times in addition to the preconcentration on the DIPHONIX® resin column. This strontium was decontaminated from any residual potassium, calcium, and trivalent ions including yttrium ($^{90}Y$ is the daughter product of $^{90}Sr$ decay).

The urine used in the methods of the present invention is pretreated to acidify the urine and remove some of the organic materials present that can interfere with scintillation prior to loading onto the DP-resin column. The pretreatment preferably involves the acidification of urine with 0.1 M MSA (introduced in neat form) followed by stirring of the acidified urine with about 1 to about 5 wt % (preferably about 1 wt %) activated carbon. After stirring for preferably at least about 1 minute (e.g., about 3 to about 5 minutes), the sample is centrifuged, e.g., at about 3500 rpm for about 15 minutes, and the supernatant is filtered through a polypropylene filter (about 0.15-0.45 μm pore size) to remove microparticles of activated carbon. This treatment achieves several objectives. At pH<2, $Sr^{2+}$ is released from the carriers that bind it in urine. Unlike nitric acid, MSA does not react with bile pigments forming strong light-absorbing products that interfere with scintillation counting. Activated carbon removes pigments and high-molecular weight compounds that can foul the ion-exchange columns. Activated carbon does not retain $Sr^{2+}$ during the treatment, provided that the pH is adjusted to less than about 2. Since the pH of urine naturally varies from 4.4 to 8 and urine has mildly buffering properties, addition of 0.1 M MSA may not result in pH<2 for some samples. In this case, the pH should be adjusted with additional MSA until the pH is less than 2.

Table 1 provides calculated values of $k_{ex}$ for DIPHONIX® resin and Sr Resin columns (for column operation under equilibrium conditions) using the reported and measured values for distribution ratios. Bed ratios of 0.30 and 0.25 were assumed for DIPHONIX® resin and Sr Resin, respectively. For the latter resin, the parameters are taken from data supplied by the manufacturer.

TABLE 1

| Resin | Acid, M | $k_{ex}$ K⁺ | $k_{ex}$ Na⁺ | $k_{ex}$ Sr²⁺ |
|---|---|---|---|---|
| DIPHONIX® + MSA | 0.10 | 17.41 | 7.71 | 721.39 |
| | 0.15 | 13.43 | 5.47 | 267.00 |
| | 0.20 | 10.95 | 2.79 | 182.42 |
| | 0.25 | 9.95 | 3.98 | 131.01 |
| | 0.40 | 8.46 | 3.13 | 49.25 |
| | 0.80 | 7.21 | 2.84 | 13.27 |
| | 1.00 | — | — | 8.36 |
| DIPHONIX® + HNO₃ | 2.0 | — | — | 3.81 |
| | 3.0 | | | 1.44 |
| | 4.0 | | | 2.87 |
| DIPHONIX® + MSA + 0.1M NaCl 0.1M KCl | 0.10 | 7.96 | 3.98 | 49.40 |
| | 0.15 | 6.97 | 3.48 | 24.53 |
| | 0.20 | 6.47 | 2.99 | 24.88 |
| | 0.25 | 5.47 | 2.74 | 19.90 |
| | 0.40 | 4.48 | 2.24 | 12.99 |
| Sr Resin + HNO₃ | 0.02 | 0.1 | 0.10 | 0.2 |
| | 0.05 | 0.1 | 0.10 | 0.7 |
| | 0.10 | 0.9 | 0.10 | 1.1 |
| | 0.30 | 1.8 | 0.20 | 6.5 |
| | 0.50 | 2.0 | 0.20 | 11 |
| | 1.00 | 3.5 | 0.30 | 30 |
| | 2.00 | 3.5 | 0.28 | 50 |
| | 4.00 | 3.0 | 0.28 | 70 |
| | 7.00 | 0.8 | 0.10 | 80 |

Table 2 provides results from theoretical modeling of DIPHONIX® resin column performance under equilibrium conditions. The load solution contains 0.1 M NaCl+0.1 M KCl in 0.1 M MSA. After elution with 0.1 M or 0.2 M MSA, the column is stripped using about 4 column volumes of 3 M $HNO_3$.

TABLE 2

| No. | FIG. | Load, column volumes | No. theor. plates | Eluent, M MSA | Eluted, column volumes | Four column volume strip using 3M HNO₃ | | |
|---|---|---|---|---|---|---|---|---|
| | | | | | | Sr conc. factor | [K], mM | % Sr recovery |
| 1 | 7 | 10 | 10 | 0.1 | 30 | 2.5 | 1.3 | 99.2 |
| 2 | 8 | 10 | 10 | 0.2 | 20 | 2.5 | 0.96 | 99.4 |
| 3 | 9 | 20 | 10 | 0.2 | 19 | 4.95 | 1.5 | 99.1 |
| 4 | 10 | 30 | 20 | 0.2 | 16 | 7.44 | 1.7 | 99.3 |

Table 3 provides minimum values of elution for column test No. 1 (FIG. 11). Estimates are for the number of column volumes required to elute $K^+$ and $Na^+$ ions after 10× column volume load on 2 mL DIPHONIX® resin column (1.5 mL/min elution).

TABLE 3

| Elution with | 0.1M MSA | 0.2M MSA |
|---|---|---|
| $K^+$ | 18 | 12 |
| $Na^+$ | 10 | 7 |

Table 4 provides trial data for column evaluation No. 2 and 3 (FIGS. 12 and 13). Both series are 0.1 M MSA load solutions eluted with 0.1 M MSA. The load was 10 column volumes (2 mL, 0.54 cm²×3.7 cm column) and the elution was to about 22 to 23 column volumes at about 1.5 mL/min.

TABLE 4

| | Ex. No. 2 aqueous matrix (FIG. 12) | | | Ex. No. 3 acidified human urine treated with charcoal (FIG. 13) | | |
|---|---|---|---|---|---|---|
| | $K^+$ | $Na^+$ | $Sr^{2+}$ | $K^+$ | $Na^+$ | $Sr^{2+}$ |
| Load, mM | 96.4 | 88.7 | 6.4 | 64.2 | 160 | 6.4 |
| Load, mmol | 1.93 | 1.77 | 0.127 | 1.19 | 2.98 | 0.061 |
| Load (effluent), mmol | 1.30 | 1.35 | 0 | 0.84 | 2.28 | 0 |
| % retained | 32.6 | 23.7 | 100 | 29.7 | 23.5 | 100 |
| Column, M | 0.315 | 0.21 | 0.064 | 0.18 | 0.35 | 0.063 |
| Recovered, mmol 3M HNO₃ strip | $4.35 \times 10^{-5}$ | $2.75 \times 10^{-3}$ | 0.125 | $1.45 \times 10^{-4}$ | $2.57 \times 10^{-3}$ | 0.108 |
| Conc. on the column after 22 volume elution | 21.5 µM | 1.38 mM | 63 mM | 73 µM | 1.29 mM | 54 mM |
| Eluent, mmol by integration | 0.56 | 0.36 | — | 0.32 | 0.57 | 0.017 |
| Sr, recovery % after 22 volume elution | | 100 | | | 86.4 | |
| Sr recovery, % after 10 volume elution | | | | | 98.0 | |

While there has been disclosed what is considered to be the preferred embodiments of the present invention, it is understood that various changes in the details may be made without departing from the spirit, or sacrificing any of the advantages of the present invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The embodiments of the invention in which an exclusive property or privilege is claimed are defined as follows:

1. A method for extracting strontium ions from urine, the method comprising the steps of:

(a) pretreating a sample of urine by acidifying the urine to a pH of less than about 2 with methanesulfonic acid and removing scintillation-interfering materials from the urine;
(b) loading a known quantity of the pretreated urine onto a preconditioned column of a diphosphonic acid-based ion-exchange resin comprising diphosphonic acid groups and sulfonic acid groups bonded to a particulate polymeric matrix;
(c) passing a flow of aqueous methanesulfonic acid through the diphosphonic acid-based ion-exchange resin, wherein the flow of aqueous methanesulfonic acid has a concentration and volume sufficient to reduce the concentration of alkali metal ions from the urine eluting from the diphosphonic acid-based ion-exchange resin to about 10 mM or less;
(d) passing a flow of aqueous nitric acid though the diphosphonic acid-based ion-exchange resin, wherein the flow of aqueous nitric acid has a concentration and volume sufficient to elute at least about 85 mole percent of any strontium ions from the urine off of the diphosphonic acid-based ion-exchange resin;
(e) directing the flow of aqueous nitric acid containing the strontium ions eluting from the diphosphonic acid-based ion-exchange resin through a column of a preconditioned strontium extraction chromatographic resin comprising a substituted 18-crown-6 crown ether adsorbed onto a porous polymeric support, to concentrate the strontium ions on the strontium extraction chromatographic resin;
(f) subsequently passing a flow of an aqueous stripping eluent through the strontium extraction chromatographic resin, wherein the stripping eluent comprises water or a dilute acid solution of less that about 0.1 M acid concentration, and has a volume sufficient to elute at least about 85 mole percent of the strontium ions from the strontium extraction chromatographic resin; and
(g) collecting the flow of aqueous stripping eluent containing the strontium ions eluting from the strontium extraction chromatographic resin;

wherein the diphosphonic acid-based ion-exchange resin is preconditioned with aqueous methanesulfonic acid having a concentration about equal to the concentration of the flow of methanesulfonic acid; and the strontium extraction chromatographic resin is preconditioned with aqueous nitric acid having a concentration about equal to the concentration of the flow of nitric acid.

2. The method of claim 1 wherein the diphosphonic acid-based ion-exchange resin comprises a particulate polystyrene/divinylbenzene matrix (beads) with diphosphonic acid and sulfonic acid groups bound to the matrix, and the strontium extraction chromatographic resin comprises about 1 M 4,4'(5')-di-tert-butylcyclohexano 18-crown-6 in 1-octanol, adsorbed onto a porous polyacrylate resin support.

3. The method of claim 1 wherein the flow of aqueous methanesulfonic acid has a methanesulfonic acid concentration of about 0.01 to 2 M and the volume of the flow of methanesulfonic acid is about 10 to about 30 column volumes.

4. The method of claim 1 wherein the flow of aqueous nitric acid has a nitric acid concentration in the range of about 1 M to about 10 M and the volume of the flow of nitric acid is about 2 to about 5 column volumes.

5. The method of claim 1 wherein the flow of aqueous stripping eluent comprises water or aqueous nitric acid having an acid concentration of about 0.1 M or less and the volume of the flow of aqueous stripping eluent is about 2 to about 5 column volumes.

6. The method of claim 1 further comprising the steps of (h) determining the total amount of strontium collected in step (g); and (i) calculating the concentration of strontium in the urine from the amount of strontium determined in step (h) and the known quantity of the urine loaded onto the diphosphonic acid-based ion-exchange resin.

7. The method of claim 1 wherein the urine is pretreated in step (a) by acidifying the urine to a pH of less than about 2 with methanesulfonic acid, agitating the acidified urine with activated carbon, and then separating the activated carbon from the acidified urine.

* * * * *